United States Patent
Ye et al.

(10) Patent No.: US 11,913,934 B2
(45) Date of Patent: Feb. 27, 2024

(54) SYSTEMS AND METHODS TO DETERMINE A CHARACTERISTIC OF A DRILLING FLUID

(71) Applicant: Halliburton Energy Services, Inc., Houston, TX (US)

(72) Inventors: Xiangnan Ye, Cypress, TX (US); Dale E. Jamison, Humble, TX (US); Marek Kozikowski, Conroe, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 224 days.

(21) Appl. No.: 17/124,191

(22) Filed: Dec. 16, 2020

(65) Prior Publication Data

US 2022/0186617 A1 Jun. 16, 2022

(51) Int. Cl.
  *G01N 33/28* (2006.01)
  *G01N 25/18* (2006.01)
  *G01N 9/36* (2006.01)

(52) U.S. Cl.
  CPC ........... *G01N 33/2847* (2013.01); *G01N 9/36* (2013.01); *G01N 25/18* (2013.01)

(58) Field of Classification Search
  CPC ...... G01N 33/2847; G01N 9/36; G01N 25/18; G01N 33/2835
  See application file for complete search history.

(56) References Cited

U.S. PATENT DOCUMENTS

| | | | |
|---|---|---|---|
| 4,441,362 A * | 4/1984 | Carlson | G01F 1/74 73/61.44 |
| 7,093,662 B2 * | 8/2006 | deBoer | E21B 33/0355 166/250.07 |
| 10,983,499 B2 * | 4/2021 | Sarmiento Klapper | E21B 21/062 |
| 2006/0173625 A1 | 8/2006 | Moran | |
| 2017/0321504 A1 * | 11/2017 | Ye | E21B 21/01 |

(Continued)

FOREIGN PATENT DOCUMENTS

| | | |
|---|---|---|
| EP | 2807483 B1 | 5/2017 |
| WO | 2021015747 A1 | 1/2021 |

OTHER PUBLICATIONS

International Search Report & Written Opinion in PCT/US2020/065588, dated Sep. 1, 2021.

(Continued)

*Primary Examiner* — Eman A Alkafawi
*Assistant Examiner* — Sangkyung Lee
(74) *Attorney, Agent, or Firm* — Barnes & Thornburg, LLP (57) ABSTRACT

Systems and methods to determine a characteristic of a drilling fluid are presented. A method to determine a characteristic of a drilling fluid includes obtaining a measurement of a mud density of a drilling fluid formed from a mixture of a plurality of components. The method also includes obtaining a measurement of a thermal conductivity of the drilling fluid and determining an error function of a calculation of characteristics of the drilling fluid, where the error function is indicative of a threshold difference between the calculation of the characteristics of the drilling fluid and the characteristics of the drilling fluid obtained from retort data of a fluid distillation process. The method further includes determining, based on the error function, an oil water ratio of the drilling fluid and an average specific gravity of the drilling fluid.

20 Claims, 4 Drawing Sheets

(56) References Cited

U.S. PATENT DOCUMENTS

| | | |
|---|---|---|
| 2018/0202246 A1 | 7/2018 | Kleinguetl et al. |
| 2020/0018147 A1 | 1/2020 | Kleinguetl et al. |
| 2020/0240221 A1 | 7/2020 | Kleinguetl et al. |

OTHER PUBLICATIONS

Lotfizadeh, et al. "A continuum Maxwell theory for the thermal conductivity of clustere nanocolloids", J Nanopart Res (2015), vol. 17, No. 6, 7 pgs.

Cheng, et al. "A Technique for Predicting the Thermal Conductivity of Suspensions, Emulsions and Porous Materials", Int. J. Heat Mass Transfer, (1970) vol. 13, pp. 537-546.

\* cited by examiner

SYSTEMS AND METHODS TO DETERMINE A CHARACTERISTIC OF A DRILLING FLUID

BACKGROUND

The present disclosure relates generally to systems and methods to determine a characteristic of a drilling fluid.

Wellbores are sometimes drilled from the surface of a wellsite several hundred to several thousand feet downhole to reach hydrocarbon resources.

During the drilling of a wellbore into a subterranean formation, a drilling fluid, also referred to as a drilling mud, may be continuously circulated from the well surface down to the bottom of the wellbore being drilled and back to the well surface again. The drilling fluid may include a mixture of water, oil, additives (e.g., viscosifiers, weighting materials, emulsifying surfactants, and the like), and combinations thereof, to impart certain properties to the drilling fluid to satisfy different drilling requirements.

Typically, a procedure called a "retort" has been used to measure the oil, water, and solids of concentration of oil-based drilling fluids. A retort uses a distillation unit to heat and then distill the oil and water in an oil-based drilling fluid. The volume fraction of each is then compared to the original known volume used during formulation of the oil-based drilling fluid in order to measure the changes to the oil-based drilling fluid during use. The solids concentration are also sometimes determined.

BRIEF DESCRIPTION OF THE DRAWINGS

Illustrative embodiments of the present disclosure are described in detail below with reference to the attached drawing figures, which are incorporated by reference herein, and wherein.

The illustrated figures are only exemplary and are not intended to assert or imply any limitation with regard to the environment, architecture, design, or process in which different embodiments may be implemented.

DETAILED DESCRIPTION

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments is defined only by the appended claims.

The present disclosure relates to systems and methods to determine a characteristic of a drilling fluid, such as the oil water ratio of the drilling fluid. The drilling fluid analysis system obtains a measurement of a mud density of a drilling fluid formed from a mixture of liquid and solid components including, for example, a mixture of water, oil, brine, barite, additives (e.g., viscosifiers, weighting materials, emulsifying surfactants, and the like), and combinations thereof. In some embodiments, the drilling fluid analysis system also determines a base oil type of the oil component of the drilling fluid. In some embodiments, the drilling fluid analysis system obtains or determines the mud density of each component of the drilling fluid, then obtains or determines the mud density of the drilling fluid based on the density of every component of the drilling fluid.

The drilling fluid analysis system also obtains a measurement of a thermal conductivity of the drilling fluid. In some embodiments, the drilling fluid analysis system obtains the thermal conductivity of each component of the drilling fluid (e.g., the thermal conductivity of water, oil, brine, and barite), and determines the measurement of the thermal conductivity of the drilling fluid based on the thermal conductivity of every component of the drilling fluid. In some embodiments, the drilling fluid analysis system also obtains a volumetric fraction of each component of the drilling fluid, where the sum of the volumetric fractions of the components is equal to 1.

The drilling fluid analysis system also determines an error function of a calculation of characteristics of the drilling fluid, where the error function is indicative of a threshold difference between the calculation of the characteristics of the drilling fluid and the characteristics of the drilling fluid obtained from retort data of a mud distillation process. In some embodiments, the error function is based on the thermal conductivity of each component of the drilling fluid. In one or more of such embodiments, the error function is partially expressed by the thermal conductivity of each component of the drilling fluid. In some embodiments, the error function is based on the volumetric fraction of the components of the drilling fluid. In one or more of such embodiments, the error function is partially expressed by the volumetric fraction of each component of the drilling fluid. In some embodiments, the drilling fluid analysis system also determines a minimum value of the error function.

The system then determines an oil water ratio of the drilling fluid and an average specific gravity of the drilling fluid based on the error function. In some embodiments, the system determines the oil water ratio of the drilling fluid based on a minimum value of the error function. In some embodiments, the system determines the average specific gravity of the drilling fluid based on the minimum of the error function. In some embodiments, the drilling fluid analysis system dynamically performs the operations described herein to determine the oil water ratio and the average specific gravity of the drilling fluid during a drilling operation. In some embodiments, during the drilling operation, the drilling fluid analysis system periodically or continuously performs operations described herein to obtain up-to-date measurements of the mud density and thermal conductivity of the drilling fluid. In some embodiments, the drilling fluid analysis system also periodically or continuously provides up-to-date values of the oil water ratio of the drilling fluid and the average specific gravity of the drilling fluid to an operator. In some embodiments, the drilling fluid analysis system also generates one or more plots of the oil water ratio of different samples of drilling fluids and provides the plots for display on an electronic display. In some embodiments, the drilling fluid analysis system also generates one or more plots of the average specific gravity of different samples of drilling fluids and provides the plots for display on an electronic display. Additional descriptions of the foregoing systems and methods to determine a characteristic of a drilling fluid are described in the paragraphs below and are illustrated in FIGS. 1-6.

Figure 1:
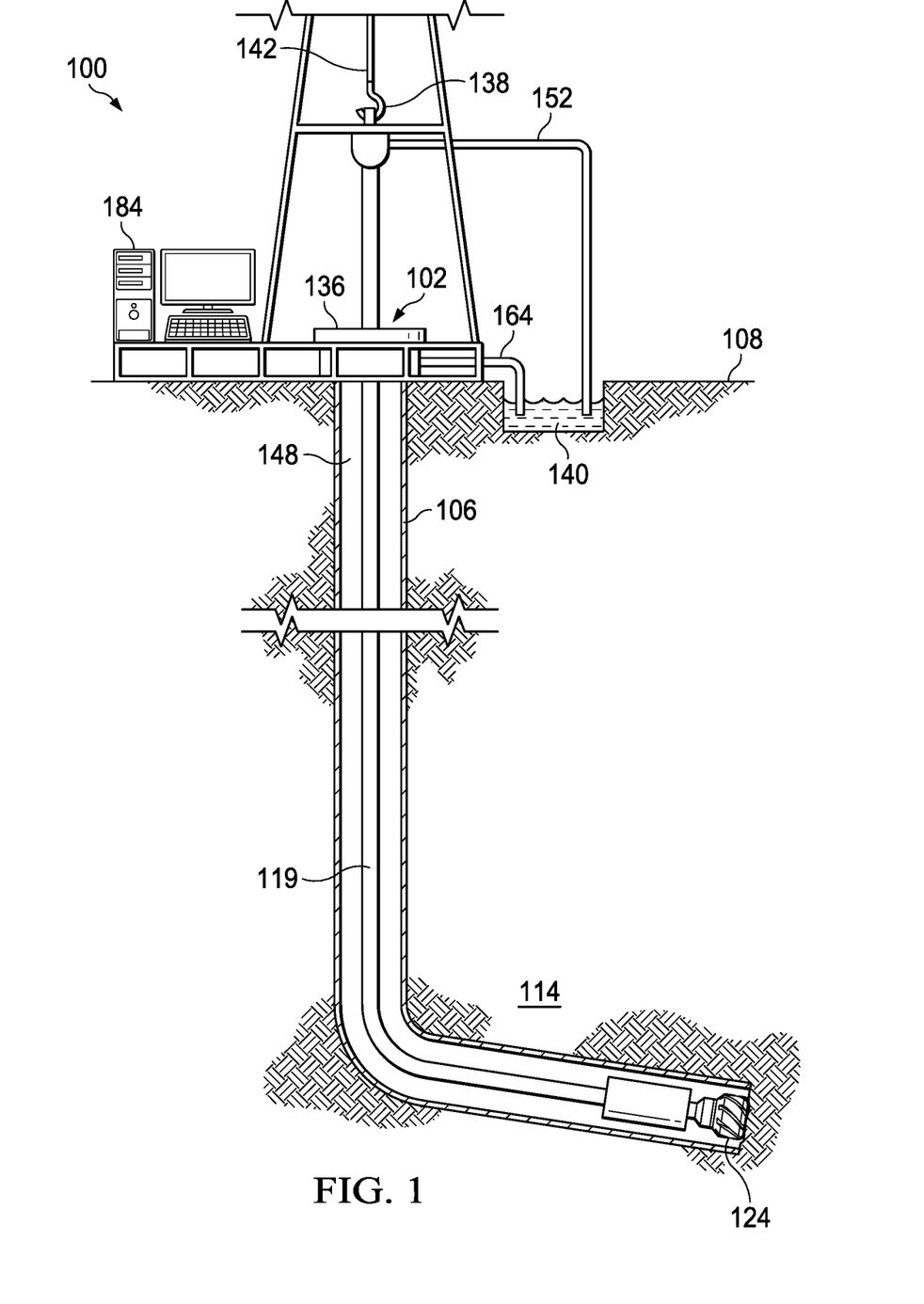
FIG. 1 is a schematic, side view of a drilling environment in which a drilling fluid analysis system is deployed.

Turning now to the figures, FIG. 1 is a schematic, side view of a drilling environment 100. In the embodiment of FIG. 1, a well 102 having a wellbore 106 extends from a surface 108 of well 102 to or through a formation 114. A hook 138, cable 142, traveling block (not shown), and hoist (not shown) are provided to lower a conveyance 119 down wellbore 106 of well 102 or to lift conveyance 119 up from wellbore 106 of well 102. In one or more embodiments, conveyance 119 may be a drill string, drill pipe, wireline, slickline, coiled tubing, production tubing, downhole tractor or another type of conveyance operable to be deployed in wellbore 106. At a wellhead 136, an inlet conduit 152 is coupled to a fluid source (not shown) to provide fluids, such as drilling fluids, downhole. In the embodiment of FIG. 1, conveyance 119 has an internal cavity that provides a fluid flow path from surface 108 to a downhole location.

In some embodiments, the fluids travel down conveyance 119 and exit conveyance 119 at a drill bit 124. The fluids flow back toward surface 108 through a wellbore annulus 148 and exit the wellbore annulus 148 via an outlet conduit 164 where the fluids are captured in container 140. In some embodiments, conveyance 119 also provides telemetry of data indicative of one or more parameters of the drilling operation and well 102. Examples of parameters of the drilling operation and well 102 include, but are not limited to, an azimuth of well 102, a dip angle of well 102, a frictional force experienced by conveyances and tools used during the drilling operation, the diameter of wellbore 106, the type of lubricity used for the drilling operation, presence of the cuttings bed in wellbore 106, presence of the pack-off, the dogleg in wellbore 106, the keyseat in wellbore 106, the degree of curvature of wellbore 106, the wellbore tortuosity of wellbore 106, the viscous effect of wellbore 106, the diameter of wellbore 106, the asperity between the conveyance used in the drilling operation and wellbore 106, as well as other parameters related to the drilling operation or well 102.

In some embodiments, sensors or transducers (not shown) are located at the lower end of conveyance 119. In one or more embodiments, sensors are built into a cylindrical drill collar that is positioned close to drill bit 124. While drilling is in progress, these sensors continuously or intermittently determine one or more parameters of the drilling operation or well 102, and transmit the information to a surface detector by one or more telemetry techniques including, but not limited to, mud pulse telemetry, acoustic telemetry, and electromagnetic wave telemetry. In one or more embodiments, where a mud-pulse telemetry system is deployed in wellbore 106 to provide telemetry, telemetry information is transmitted by adjusting the timing or frequency of viable pressure pulses in the drilling fluid that is circulated through conveyance 119 during drilling operations. In one or more embodiments, an acoustic telemetry system that transmits data via vibrations in the tubing wall of conveyance 119 is deployed in wellbore 106 to provide telemetry. More particularly, the vibrations are generated by an acoustic transmitter (not shown) mounted on conveyance 119 and propagate along conveyance 119 to an acoustic receiver (not shown) also mounted on conveyance 119. In one or more embodiments, an electromagnetic wave telemetry system that transmits data using current flows induced in conveyance 119 is deployed in wellbore 106 to provide telemetry. Additional types of telemetry systems may also be deployed in wellbore 106 to transmit data from tools (not shown) and other downhole components to drilling fluid analysis system 184.

In some embodiments, a surface-based electronic device, such as drilling fluid analysis system 184, includes one or more processors configured to obtain a measurement of a mud density of a drilling fluid formed from a mixture of a plurality of components and obtain a measurement of a thermal conductivity of the drilling fluid.

In some embodiments, the thermal conductivity of the drilling fluid is expressed by the following equation:

$$TC = \sum_{i=1}^{x} f(TC_i, V_i) \quad \text{Equation 1}$$

where TC is the thermal conductivity of the drilling fluid, $TC_i$ is the thermal conductivity of a component of the drilling fluid, x is the total number of components of the drilling fluid, and $V_i$ is the volumetric fraction of a component of the drilling fluid, where the sum of the volumetric fractions of all of the components of the drilling fluid is equal to 1. In an exemplary embodiment where the drilling fluid has four components, such as water, oil, a low gravity solid such as brine, and a high gravity solid such as barite, the value of x is equal to 4, and equation 1 becomes the following:

$$TC = \sum_{i=1}^{4} f(TC_i, V_i) \quad \text{Equation 2}$$

where TC is the thermal conductivity of the drilling fluid, $TC_i$ is the thermal conductivity of a component of the drilling fluid, 4 is the total number of components of the drilling fluid, and $V_i$ is the volumetric fraction of a component of the drilling fluid, where the sum of the volumetric fractions of all of the components of the drilling fluid is equal to 1.

In some embodiments, the thermal conductivity and/or the volumetric fraction of each component is obtained from a database of existing thermal conductivities of the different components of a drilling fluid. In some embodiments, the thermal conductivity and/or the volumetric fraction of each component is periodically and/or continuously measured before the drilling fluid is pumped into well 102, while the drilling fluid is flowing in wellbore 106, and/or after the drilling fluid is extracted from well 102.

In some embodiments, drilling fluid analysis system 184 also determines the density of the drilling fluid, which is expressed by the following equation:

$$\rho = \sum_{i=1}^{x} f(\rho_i, V_i) \quad \text{Equation 3}$$

where $\rho$ is the density of the drilling fluid, $\rho_i$ is the density of a component of the drilling fluid, x is the number of components of the drilling fluid, and $V_i$ is the volumetric fraction of a component of the drilling fluid, where the sum of the volumetric fractions of all of the components of the drilling fluid is equal to 1.

Continuing with the foregoing example, where the drilling fluid has four components, equation 3 becomes the following:

$$\rho = \Sigma_{i=1}^{4} f(\rho_i, V_i)$$ Equation 4 where ρ is the density of the drilling fluid, $\rho_i$ is the density of a component of the drilling fluid, 4 is the number of components of the drilling fluid, and $V_i$ is the volumetric fraction of a component of the drilling fluid, where the sum of the volumetric fractions of all of the components of the drilling fluid is equal to 1.

Further, the oil water ratio and the average specific gravity of the drilling fluid are expressed by the following equations:

$$OWR = f(V_{water}, \rho)$$ Equation 5 where OWR is the oil water ratio of the drilling fluid, $V_{water}$ is the volumetric fraction of water, and p is the density of the drilling fluid.

$$ASG = f(V_{HGS}, \rho)$$ Equation 6 where ASG is the average specific gravity of the drilling fluid, and $V_{HGS}$ is the volumetric fraction of a high gravity solid component of the drilling fluid, such as barite, and ρ is the density of the drilling fluid.

In some embodiments, the calculated oil water ratio and the average specific gravity of the drilling fluid are expressed by the following equations:

$$OWR = V_{oil}(V_{oil} + V_{water})$$ Equation 7 where $V_{oil}$ is the volumetric fraction of the oil component of the drilling fluid, and $V_{water}$ is the volumetric fraction of the water component of the drilling fluid, and $$ASG = (\rho_{HGS} \times V_{HGS} + \rho_{LGS} \times V_{LGS})/(V_{HGS} + V_{LGS})$$ Equation 8 where $\rho_{HGS}$ is the density of the high gravity solid component of the drilling fluid, $\rho_{LGS}$ is the density of the low gravity solid component of the drilling fluid, such as brine, $V_{LGS}$ is the volumetric fraction of the low gravity solid component of the drilling fluid, and $V_{HGS}$ is the volumetric fraction of a high gravity solid component of the drilling fluid.

Drilling fluid analysis system 184 also determines an error function of a calculation of characteristics of the drilling fluid, such as the oil water ratio and the average specific gravity of the drilling fluid, where the error function is indicative of a difference between the calculated characteristics of the drilling fluid and corresponding characteristics of the drilling fluid obtained from retort data of a mud distillation process. Continuing with the foregoing example, where the drilling fluid is a mixture of oil, water, a high gravity solid component and a low gravity solid component, the error function is expressed by the following equation:

$$ER = |TC - \Sigma_{i=1}^{4} f(TC_i, V_i)| + |\rho - \Sigma_{i=1}^{4} f(\rho_i, V_i)| + |OWR - V_{water}, \rho)| + |ASG - f(V_{HGS}, \rho)|$$ Equation 9 where ER is the total error.

Drilling fluid analysis system 184 also determines, based on the error function, an oil water ratio of the drilling fluid and an average specific gravity of the drilling fluid. In some embodiments, drilling fluid analysis system 184 determines values of the oil water ratio and the average specific gravity of the drilling fluid that generate a minimum error of the error function, and designates values of the oil water ratio and the average specific gravity of the drilling fluid that generate the minimum error as the values of the oil water ratio and the average specific gravity of the drilling fluid. In some embodiments, drilling fluid analysis system 184 also determines values of the oil water ratio and the average specific gravity of the drilling fluid that generate an error that is at or below a threshold error value, and designates values of the oil water ratio and the average specific gravity of the drilling fluid that generate an error that is at or below the threshold error value as the values of the oil water ratio and the average specific gravity of the drilling fluid. Additional examples of error functions and error values are provided in the paragraphs below and are illustrated in at least FIGS. 2-4.

In some embodiments, drilling fluid analysis system 184 periodically and/or continuously performs the foregoing operations to determine the oil water ratio and the average specific gravity of different samples of drilling fluids during a drilling operation. In some embodiments, drilling fluid analysis system 184 generates plots of the oil water ratio and the average specific gravity of different samples of drilling fluids, and provides the plots for display to an operator during the drilling operation. Additional descriptions of the processors and operations performed by the processors are described in the paragraphs below. Although FIG. 1 illustrates drilling fluid analysis system 184 as a surface-based electronic device that is located near well 102, in some embodiments, drilling fluid analysis system 184 is located downhole or is located in another surface-based location remote from well 102. In some embodiments, operations performed by drilling fluid analysis system 184 and described herein are performed on samples of drilling fluids before or after a drilling operation.

Figure 2:
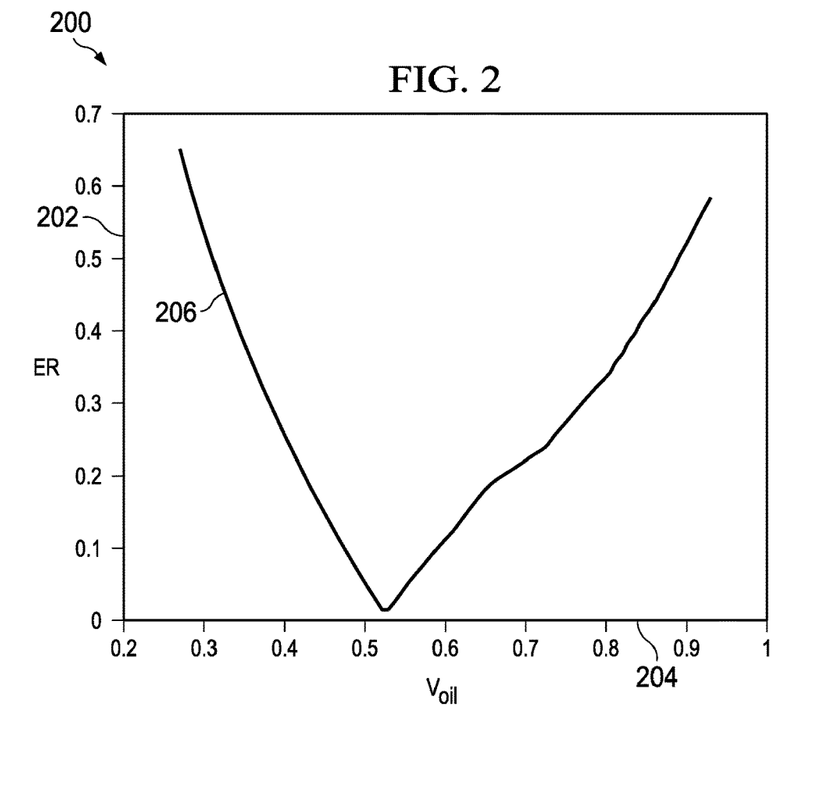
FIG. 2 is a plot of an error in determining the volumetric fraction of an oil component of a drilling fluid as a function of the volumetric fraction of an oil.

FIG. 2 is a plot 200 of an error in determining the volumetric fraction of an oil component of a drilling fluid as a function of volumetric fraction of the oil component. In the embodiment of FIG. 2, axis 202 represents values of the error, which is the difference between the predicted volumetric fraction of the oil component of the drilling fluid and the volumetric fraction of the oil component obtained from retort data of a mud distillation process. Further, axis 204 represents different values of volumetric fraction of the oil component relative to the drilling fluid. Line 206 represents values of the error function at different errors and volumetric fractions of the oil component. In one or more embodiments, line 206 is determined by solving for Equation 9 for different values of the volumetric fraction of the oil component. In one or more of such embodiments, the value of the volumetric fraction of the oil component having a minimum error (e.g., approximately 0.528) is selected. In one or more of such embodiments, a value from a range of values of the volumetric fraction of the oil component having an error that is at or below a threshold value (e.g., below 0.1, 0.05, or another threshold value) is selected.

Figure 3:
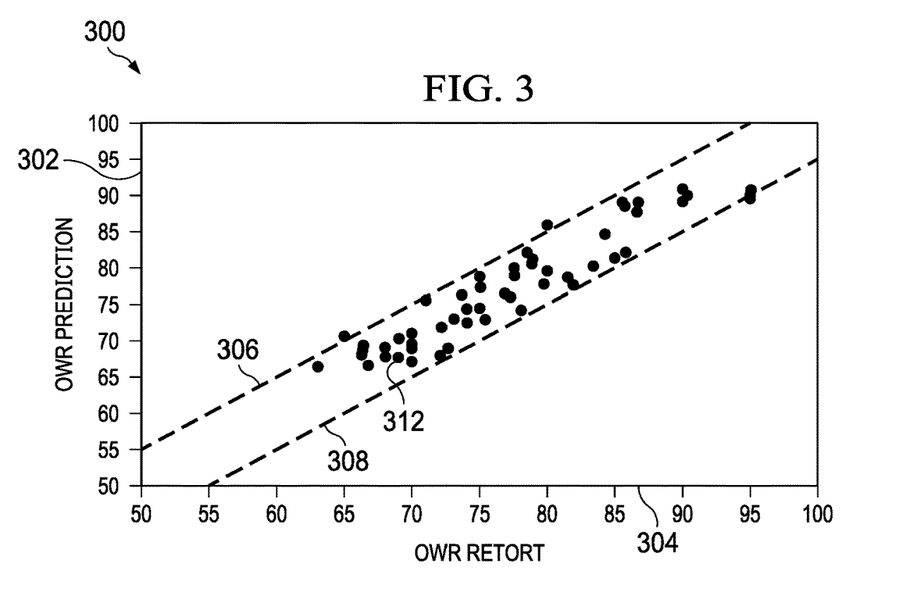
FIG. 3 is a plot of oil water ratios of different samples of drilling fluids determined by the drilling fluid analysis system of FIG. 1 compared to the oil water ratio of the samples of drilling fluids obtained from retort data of the samples of drilling fluids.

FIG. 3 is a plot 300 of oil water ratios of different samples of drilling fluids as determined by drilling fluid analysis system 184 of FIG. 1 compared to the oil water ratio of the samples of drilling fluids obtained from retort data of the samples of drilling fluids. In the embodiment of FIG. 3, axis 302 represents predictions of the oil water ratio, whereas axis 304 represents values of the oil water ratio obtained from the retort data. Further, dash lines 306 and 308 represent boundaries where an error between the predicted oil water ratio and the oil water ratio obtained from the retort data is within ±5, respectively. Further, dots, including dot 312, represent samples of drilling fluids where operations described herein are performed to predict the oil water ratio of the respective samples are compared with the retort data on the respective samples. As illustrated in FIG. 3, almost all samples fall within an error of ±5. In some embodiments, drilling fluid analysis system 184 of FIG. 1 dynamically generates plot 300 during a drilling operation and provides plot 300 for display on a display of an operator. In one or more of such embodiments, drilling fluid analysis system 184 of FIG. 1 dynamically updates plot 300 and periodically or continuously provides an up-to-date version of plot 300 for display on the display of the operator.

Figure 4:
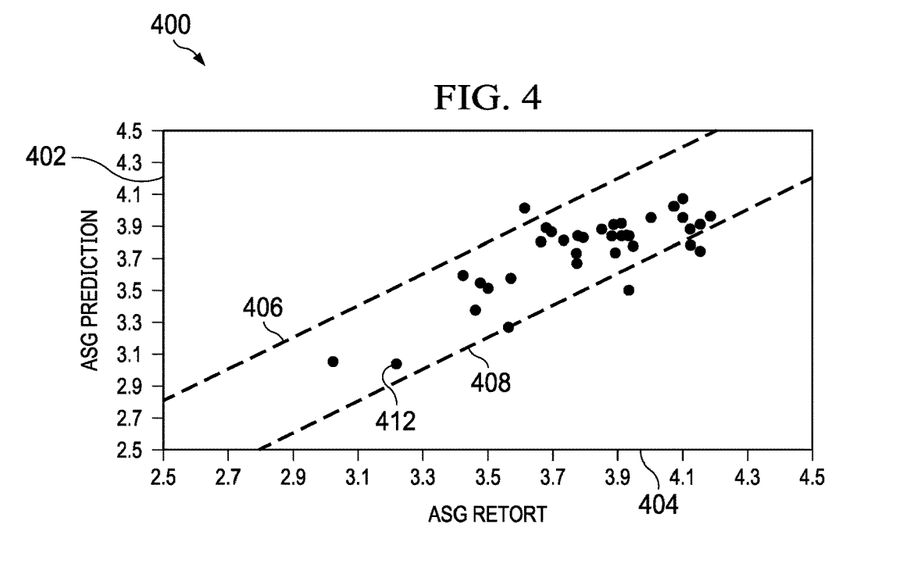
FIG. 4 is a plot of average specific gravity determined by the drilling fluid analysis system of FIG. 1 compared to the average specific gravity of the samples of drilling fluids obtained from retort data of the samples of drilling fluids.

FIG. 4 is a plot 400 of average specific gravity determined by drilling fluid analysis system 184 of FIG. 1 compared to the average specific gravity of the samples of drilling fluids obtained from retort data of the samples of drilling fluids. In the embodiment of FIG. 4, axis 402 represents predictions of the average specific gravity, whereas axis 404 represent values of the average specific gravity obtained from the retort data. Further, dash lines 406 and 408 represent boundaries where an error between the predicted average specific gravity and average specific gravity obtained from the retort data is within ±0.3, respectively. Further, dots, including dot 412, represent samples of drilling fluids where operations described herein are performed to predict the average specific gravity of the respective samples are compared with the retort data on the respective samples. As illustrated in FIG. 3, almost all samples fall within an error of ±0.3. In some embodiments, drilling fluid analysis system 184 of FIG. 1 dynamically generates plot 400 during a drilling operation and provides plot 400 for display on a display of an operator. In one or more of such embodiments, drilling fluid analysis system 184 of FIG. 1 dynamically updates plot 400 and periodically or continuously provides an up-to-date version of plot 400 for display on the display of the operator.

Figure 5:
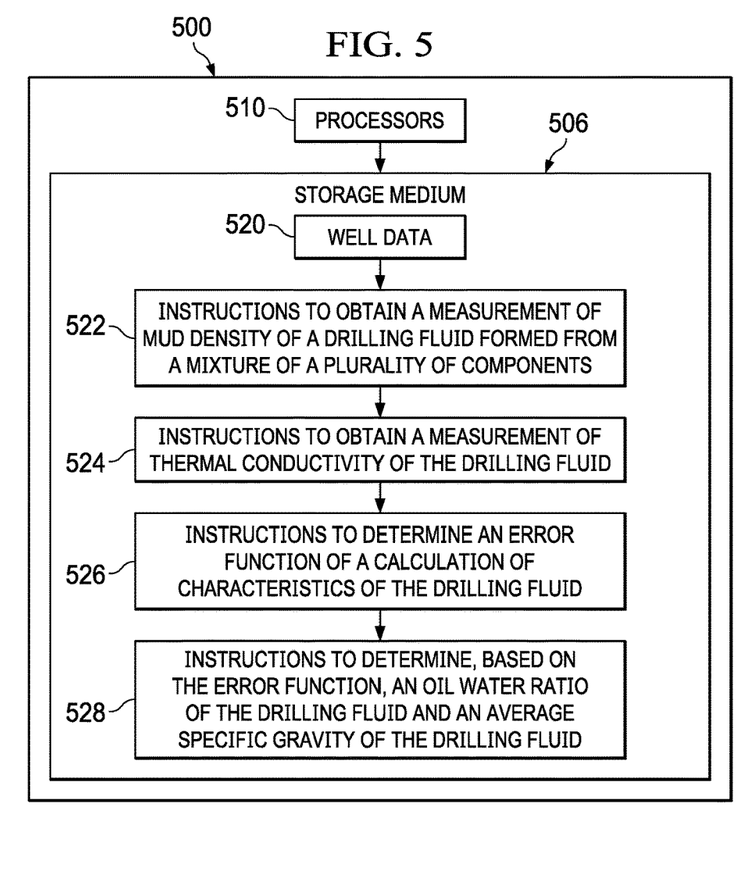
FIG. 5 is a block diagram of a drilling fluid analysis system.

FIG. 5 is a block diagram of a drilling fluid analysis system 500. Drilling fluid analysis system 500 includes a storage medium 506 and processors 510. Storage medium 506 may be formed from data storage components such as, but not limited to, read-only memory (ROM), random access memory (RAM), flash memory, magnetic hard drives, solid-state hard drives, CD-ROM drives, DVD drives, floppy disk drives, as well as other types of data storage components and devices. In some embodiments, storage medium 506 includes multiple data storage devices. In further embodiments, the multiple data storage devices may be physically stored at different locations. Drilling fluid data, which include, data indicative of measured characteristics of samples of drilling fluids, components of the samples of drilling fluids, properties of the samples of drilling fluids, and retort data on the samples of drilling fluids as well as other types of drilling fluids and components of drilling fluids, are stored at a first location 520 of storage medium 506. As shown in FIG. 5, instructions to obtain a measurement of a mud density of the drilling fluid are stored at a second location 522 of storage medium 506, instructions to obtain a measurement of a thermal conductivity of the drilling fluid are stored at a third location 524 of the storage medium 506, instructions to determine an error function of a calculation of characteristics of the drilling fluid are stored at a fourth location 526 of storage medium 506, and instructions to determine, based on the error function, an oil water ratio of the drilling fluid and an average specific gravity of the drilling fluid are stored at a fifth location 528 of storage medium 506. The instructions to perform other operations described herein are also stored in the storage medium 506.

In some embodiments, drilling fluid analysis system 500 is a component of drilling fluid analysis system 184 of FIG. 1, or a component of another surface-based electronic device. In some embodiments, drilling fluid analysis system 500 is formed from drilling fluid analysis system 184 of FIG. 1, or from other surface-based electronic devices. In further embodiments, drilling fluid analysis system 500 is a component of a downhole tool that is deployed in wellbore 106 of FIG. 1. In further embodiments, parts of drilling fluid analysis system 500 are deployed on a surface-based electronic device, such as drilling fluid analysis system 184 of FIG. 1, and parts of drilling fluid analysis system 500 are deployed downhole.

Figure 6:
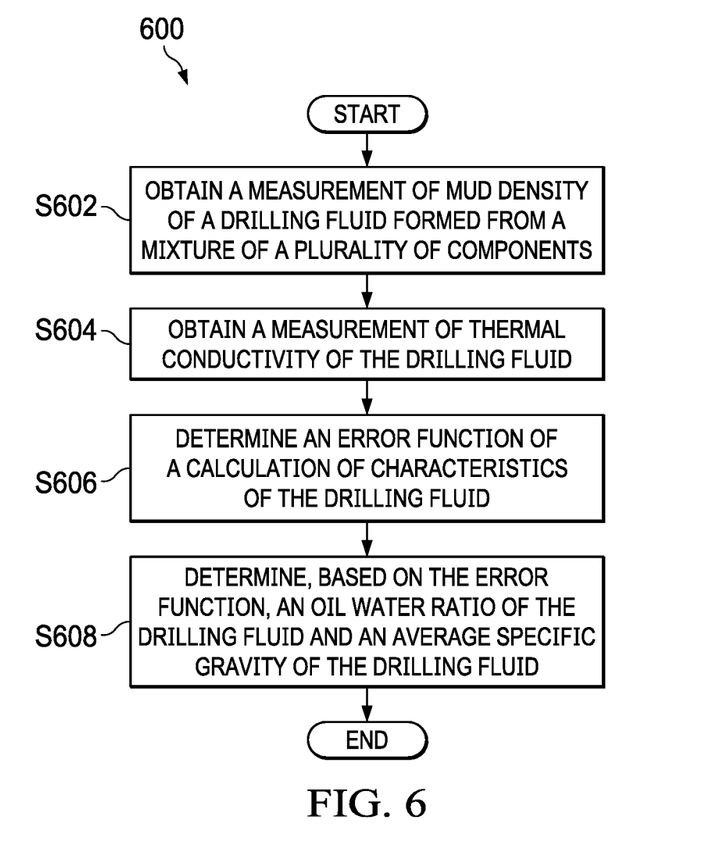
FIG. 6 is a flow chart of a process to determine a characteristic of a drilling fluid.

FIG. 6 is a flow chart of a process 600 to determine a characteristic of a drilling fluid. Although the operations in the process 600 are shown in a particular sequence, certain operations may be performed in different sequences or at the same time where feasible. Further, although the operations in process 600 are described to be performed by processors 510 of drilling fluid analysis system 500 of FIG. 5, the operations may also be performed by one or more processors of other electronic devices operable to perform operations described herein.

At block S602, a measurement of a mud density of a drilling fluid formed from a mixture of a plurality of components is obtained by drilling fluid analysis system 184. Examples of different components of a drilling fluid include, but are not limited to, oil, water, brine, and barite. In the embodiment of FIG. 1, for example, measurements of a mud density of a drilling fluid pumped into wellbore 106 during a drilling operation are obtained by drilling fluid analysis system 184. In some embodiments, a base oil type of an oil component of the drilling fluid is also determined, and one or more operations performed to determine a characteristic of the drilling fluid is based on the oil type of the oil component of the drilling fluid. At block S604, a measurement of a thermal conductivity of the drilling fluid is obtained. In the embodiment of FIG. 1, for example, measurements of the thermal conductivity of samples of drilling fluid are obtained by drilling fluid analysis system 184. In some embodiments, the thermal conductivity of samples of drilling fluid are measured on the surface or by a downhole device while the samples of drilling fluid are downhole. In some embodiments, the thermal conductivity of samples of drilling fluid are obtained from retort data of previously-measured drilling fluids. In some embodiments, the thermal conductivity of each component of the drilling fluid is measured or is obtained, and the thermal conductivity of the drilling fluid is determined based on the thermal conductivity of the individual components of the drilling fluid. In some embodiments, a volumetric fraction of each component of the drilling fluid is obtained, where the sum of the volumetric fractions of the components of the drilling fluid is equal to 1. In one or more of such embodiments, the thermal conductivity of the drilling fluid is obtained based on the volumetric fraction of the different components of the drilling fluid.

At block S606, an error function of a calculation of characteristics of the drilling fluid is determined. In the embodiment of FIG. 1, for example, the error function is calculated by drilling fluid analysis system 184. In some embodiments, the error function is based on or is partially defined by the thermal conductivity of individual components of the drilling fluid. In some embodiments, the error function is based on or is partially defined by the volumetric fraction of the individual components of the drilling fluid. At block S608, an oil water ratio of the drilling fluid and an average specific gravity of the drilling fluid are determined based on the error function. In the embodiment of FIG. 1, drilling fluid analysis system 184 solves equations 1-9 to determine oil water ratios and average specific densities of samples of the drilling fluid based on an error function expressed by equation 9. In some embodiments, a minimum value of the error function is determined, and a value of the oil water ratio and a value of the average specific gravity of the drilling fluid that generate the minimum value of the error function are designated as the value of the oil water ratio and the value of the average specific gravity of the drilling fluid, respectively. In some embodiments, a threshold error value is obtained, and a value of the oil water ratio and a value of the average specific gravity of the drilling fluid that generate an error that is at or below the threshold error value are designated as the value of the oil water ratio and the value of the average specific gravity of the drilling fluid, respectively.

In some embodiments, where up-to-date characteristics of the drilling fluid are periodically or continuously assessed and the process returns to block S602, and the operations described herein are performed to obtain the up-to-date characteristics of the drilling fluid. In some embodiments, where characteristics of different drilling fluids (such as different samples of drilling fluids that formed from different mixtures of solid and liquid components) are determined, the process also returns to block S602, and the operations described herein are performed to obtain characteristics of newly sampled drilling fluid. In some embodiments, values of the oil water ratio and the average specific gravity of the drilling fluid are provided for display on an electronic device of an operator. In some embodiments, plots of the oil water ratio and the average specific gravity of the drilling fluid (such as plots illustrated in FIGS. 3 and 4) are generated, and are provided for display an on an electronic device of the operator. In some embodiments, data indicate of values obtains by processes described herein are stored in a database, such as storage medium 506 of FIG. 5.

The above-disclosed embodiments have been presented for purposes of illustration and to enable one of ordinary skill in the art to practice the disclosure, but the disclosure is not intended to be exhaustive or limited to the forms disclosed. Many insubstantial modifications and variations will be apparent to those of ordinary skill in the art without departing from the scope and spirit of the disclosure. For instance, although the flowcharts depict a serial process, some of the steps/processes may be performed in parallel or out of sequence, or combined into a single step/process. The scope of the claims is intended to broadly cover the disclosed embodiments and any such modification. Further, the following clauses represent additional embodiments of the disclosure and should be considered within the scope of the disclosure.

Clause 1, a computer-implemented method to determine a characteristic of a drilling fluid, comprising: obtaining a measurement of a mud density of a drilling fluid formed from a mixture of a plurality of components; obtaining a measurement of a thermal conductivity of the drilling fluid; determining an error function of a calculation of characteristics of the drilling fluid, wherein the error function is indicative of a threshold difference between the calculation of the characteristics of the drilling fluid and the characteristics of the drilling fluid obtained from retort data of a mud distillation process; and determining, based on the error function, an oil water ratio of the drilling fluid and an average specific gravity of the drilling fluid.

Clause 2, the computer-implemented method of clause 1, further comprising determining a base oil type of an oil used in the drilling fluid, wherein the oil is one component of the plurality of components of the drilling fluid.

Clause 3, the computer-implemented method of clauses 1 or 2, wherein obtaining the thermal conductivity of the drilling fluid comprises obtaining a thermal conductivity of each component of the drilling fluid, wherein the error function is based on the thermal conductivity of each component of the drilling fluid.

Clause 4, the computer-implemented method of clause 3, wherein the plurality of components of the drilling fluid comprise oil, water, brine, and barite, and wherein obtaining the thermal conductivity of each component of the drilling fluid comprises obtaining the thermal conductivity of oil, water, brine, and barite.

Clause 5, the computer-implemented method of clauses 3 or 4, wherein obtaining the thermal conductivity of the drilling fluid comprises obtaining a volumetric fraction of each component of the drilling fluid, wherein the error function is based on the volumetric fraction of each component of the drilling fluid, wherein a sum of the volumetric fractions of the plurality of components is equal to 1.

Clause 6, the computer-implemented method of any of clauses 1-5, wherein obtaining the mud density of each component of the drilling fluid, wherein the mud density of the drilling fluid is based on the mud density of each component of the drilling fluid.

Clause 7, the computer-implemented method of any of clauses 1-6, further comprising determining a minimum value of the error function, wherein determining, based on the error function, the oil water ratio of the drilling fluid comprises determining the oil water ratio of the drilling fluid at the minimum value of the error function.

Clause 8, the computer-implemented method of any of clauses 1-7, wherein the oil water ratio of the drilling fluid and the average specific gravity of the drilling fluid are dynamically determined during a drilling process where the drilling fluid is pumped into a wellbore.

Clause 9, the computer-implemented method of clause 8, further comprising: obtaining a second mud density of the drilling fluid; obtaining a second measurement of the thermal conductivity of the drilling fluid; determining a second error function of a second calculation of characteristics of the drilling fluid, wherein the second error function is indicative of a threshold difference between the second calculation of the characteristics of the drilling fluid and the characteristics of the drilling fluid obtained through the retort data of the mud distillation process; and determining, based on the error function, an second oil water ratio of the drilling fluid and a second average specific gravity of the drilling fluid.

Clause 10, the computer-implemented method of clause 9, further comprising dynamically providing most up-to-date values of the oil water ratio of the drilling fluid and an average specific gravity of the drilling fluid for display on an electronic display.

Clause 11, the computer-implemented method of any of clauses 1-10, further comprising: generating a plot of the oil water ratio of the drilling fluid relative to a second oil water ratio of the drilling fluid obtained from the retort data; and providing the plot for display on an electronic display.

Clause 12, the computer-implemented method of any of clauses 1-11, further comprising: generating a plot of the average specific gravity of the drilling fluid relative to a second average specific gravity of the drilling fluid obtained from the retort data; and providing the plot for display on an electronic display.

Clause 13, a system to determine a characteristic of a drilling fluid, comprising: memory; and at least one processor configured to: determine a base oil type of an oil used in a drilling fluid formed from a mixture of a plurality of components; obtain a measurement of a mud density of the drilling fluid; obtain a measurement of a thermal conductivity of the drilling fluid; determine an error function of a calculation of characteristics of the drilling fluid, wherein the error function is indicative of a threshold difference between the calculation of the characteristics of the drilling fluid and the characteristics of the drilling fluid obtained from retort data of a mud distillation process; and determine, based on the error function, an oil water ratio of the drilling fluid and an average specific gravity of the drilling fluid.

Clause 14, the system of clause 13, wherein the one or more processors are further configured to: obtain a thermal conductivity of each component of the drilling fluid; and determine error function based on the thermal conductivity of each component of the drilling fluid.

Clause 15, the system of clause 14, wherein the plurality of components of the drilling fluid comprise oil, water, brine, and barite.

Clause 16, the system of clauses 14 or 15, wherein the one or more processors are further configured to: obtain a volumetric fraction of each component of the drilling fluid, wherein the error function is based on the volumetric fraction of each component of the drilling fluid, and wherein a sum of the volumetric fractions of the plurality of components is equal to 1.

Clause 17, The system of any of clauses 13-16, wherein the one or more processors are further configured to: determine a minimum value of the error function; and determine, the oil water ratio of the drilling fluid at the minimum value of the error function.

Clause 18, a non-transitory computer-readable medium containing one or more instructions, which when executed by a processor, cause the processor to perform operations comprising: determining a base oil type of an oil used in a drilling fluid formed from a mixture of a plurality of components; obtaining a measurement of a mud density of the drilling fluid; obtain a measurement of a thermal conductivity of the drilling fluid; determining an error function of a calculation of characteristics of the drilling fluid, wherein the error function is indicative of a threshold difference between the calculation of the characteristics of the drilling fluid and the characteristics of the drilling fluid obtained from retort data of a mud distillation process; and determining, based on the error function, an oil water ratio of the drilling fluid and an average specific gravity of the drilling fluid.

Clause 19, the non-transitory computer-readable medium of clause 18, wherein the one or more instructions, which when executed by the processor cause the processor to perform operations comprising: obtaining a thermal conductivity of each component of the drilling fluid; and determining error function based on the thermal conductivity of each component of the drilling fluid.

Clause 20, the non-transitory computer-readable medium of clauses 18 or 19, wherein the one or more instructions, which when executed by the processor cause the processor to perform operations comprising: obtaining a second mud density of the drilling fluid; obtaining a second measurement of the thermal conductivity of the drilling fluid; determining a second error function of a second calculation of characteristics of the drilling fluid, wherein the second error function is indicative of a threshold difference between the second calculation of the characteristics of the drilling fluid and the characteristics of the drilling fluid obtained through the retort data of the mud distillation process; and determining, based on the error function, an second oil water ratio of the drilling fluid and a second average specific gravity of the drilling fluid.

As used herein, the singular forms "a," "an," and "the" are intended to include the plural forms as well, unless the context clearly indicates otherwise. It will be further understood that the terms "comprise" and/or "comprising," when used in this specification and/or in the claims, specify the presence of stated features, steps, operations, elements, and/or components, but do not preclude the presence or addition of one or more other features, steps, operations, elements, components, and/or groups thereof. In addition, the steps and components described in the above embodiments and figures are merely illustrative and do not imply that any particular step or component is a requirement of a claimed embodiment.

What is claimed is:

1. A computer-implemented method to determine a characteristic of a drilling fluid, comprising:
   obtaining a measurement of a mud density of a drilling fluid formed from a mixture of a plurality of components;
   obtaining a measurement of a thermal conductivity of the drilling fluid;
   obtaining a volumetric fraction of each component of the drilling fluid;
   determining an error function of a calculation of characteristics of the drilling fluid, wherein the characteristics of the drilling fluid consist of the mud density of the drilling fluid, the thermal conductivity of the drilling fluid, and the volumetric fraction of the components of the drilling fluid; wherein the mud density of the drilling fluid is based on the density of every component of the drilling fluid; wherein the measurement of the thermal conductivity of the drilling fluid is based on the thermal conductivity of every component of the drilling fluid; wherein a sum of the volumetric fraction of each of the components of the drilling fluid is equal to 1; wherein the error function is indicative of a threshold difference between the calculation of the characteristics of the drilling fluid and the characteristics of the drilling fluid obtained from retort data of a mud distillation process; wherein the thermal conductivity and the volumetric fraction of each component is continuously measured before the drilling fluid is pumped into a wellbore, while the drilling fluid is flowing in the wellbore, and after the drilling fluid is extracted from the wellbore;
   determining, based on the error function, an oil water ratio of the drilling fluid and an average specific gravity of the drilling fluid periodically or continuously during a drilling operation; and
   providing the oil water ratio of the drilling fluid and an average specific gravity of the drilling fluid to an operator during the drilling operation.

2. The computer-implemented method of claim 1, further comprising determining a base oil type of an oil used in the drilling fluid, wherein the oil is one component of the plurality of components of the drilling fluid.

3. The computer-implemented method of claim 1, wherein the components of the drilling fluid comprise oil, water, brine, and barite, and wherein obtaining the thermal conductivity of each component of the drilling fluid comprises obtaining the thermal conductivity of oil, water, brine, and barite.

4. The computer-implemented method of claim 1, further comprising determining a minimum value of the error function, wherein determining, based on the error function, the oil water ratio of the drilling fluid comprises determining the oil water ratio of the drilling fluid at the minimum value of the error function.

5. The computer-implemented method of claim 1, wherein the oil water ratio of the drilling fluid and the average specific gravity of the drilling fluid are dynamically determined during a drilling process where the drilling fluid is pumped into the wellbore.

6. The computer-implemented method of claim 5, further comprising:
obtaining a second mud density of the drilling fluid;
obtaining a second measurement of the thermal conductivity of the drilling fluid;
determining a second error function of a second calculation of characteristics of the drilling fluid, wherein the second error function is indicative of a threshold difference between the second calculation of the characteristics of the drilling fluid and the characteristics of the drilling fluid obtained through the retort data of the mud distillation process; and
determining, based on the error function, a second oil water ratio of the drilling fluid and a second average specific gravity of the drilling fluid.

7. The computer-implemented method of claim 6, further comprising dynamically providing most up-to-date values of the oil water ratio of the drilling fluid and an average specific gravity of the drilling fluid for display on an electronic display.

8. The computer-implemented method of claim 1, further comprising:
generating a plot of the oil water ratio of the drilling fluid relative to a second oil water ratio of the drilling fluid obtained from the retort data; and
providing the plot for display on an electronic display.

9. The computer-implemented method of claim 1, further comprising:
generating a plot of the average specific gravity of the drilling fluid relative to a second average specific gravity of the drilling fluid obtained from the retort data; and
providing the plot for display on an electronic display.

10. A system to determine a characteristic of a drilling fluid, comprising:
memory; and
at least one processor configured to:
determine a base oil type of an oil used in a drilling fluid formed from a mixture of a plurality of components;
obtain a measurement of a mud density of the drilling fluid;
obtain a measurement of a thermal conductivity of the drilling fluid;
obtain a volumetric fraction of each component of the drilling fluid;
determine an error function of a calculation of characteristics of the drilling fluid, wherein the characteristics of the drilling fluid consist of the mud density of the drilling fluid, the thermal conductivity of the drilling fluid, and the volumetric fraction of the components of the drilling fluid; wherein the mud density of the drilling fluid is based on the density of every component of the drilling fluid; wherein the measurement of the thermal conductivity of the drilling fluid is based on the thermal conductivity of every component of the drilling fluid; wherein a sum of the volumetric fraction of each of the components of the drilling fluid is equal to 1; wherein the error function is indicative of a threshold difference between the calculation of the characteristics of the drilling fluid and the characteristics of the drilling fluid obtained from retort data of a mud distillation process; wherein the thermal conductivity and the volumetric fraction of each component is continuously measured before the drilling fluid is pumped into a wellbore, while the drilling fluid is flowing in the wellbore, and after the drilling fluid is extracted from the wellbore;
determine, based on the error function, an oil water ratio of the drilling fluid and an average specific gravity of the drilling fluid periodically or continuously during a drilling operation; and
provide the oil water ratio of the drilling fluid and an average specific gravity of the drilling fluid to an operator during the drilling operation.

11. The system of claim 10, wherein the plurality of components of the drilling fluid comprise oil, water, brine, and barite.

12. The system of claim 10, wherein the one or more processors are further configured to:
determine a minimum value of the error function; and
determine, the oil water ratio of the drilling fluid at the minimum value of the error function.

13. A non-transitory computer-readable medium containing one or more instructions, which when executed by a processor, cause the processor to perform operations comprising:
determining a base oil type of an oil used in a drilling fluid formed from a mixture of a plurality of components;
obtaining a measurement of a mud density of the drilling fluid;
obtain a measurement of a thermal conductivity of the drilling fluid;
obtain a volumetric fraction of each component of the drilling fluid;
determining an error function of a calculation of characteristics of the drilling fluid, wherein the characteristics of the drilling fluid consist of the mud density of the drilling fluid, the thermal conductivity of the drilling fluid, and the volumetric fraction of the components of the drilling fluid; wherein the mud density of the drilling fluid is based on the density of every component of the drilling fluid; wherein the measurement of the thermal conductivity of the drilling fluid is based on the thermal conductivity of every component of the drilling fluid; wherein a sum of the volumetric fraction of each of the components of the drilling fluid is equal to 1; wherein the error function is indicative of a threshold difference between the calculation of the characteristics of the drilling fluid and the characteristics of the drilling fluid obtained from retort data of a mud distillation process; wherein the thermal conductivity and the volumetric fraction of each component is continuously measured before the drilling fluid is pumped into a wellbore, while the drilling fluid is flowing in the wellbore, and after the drilling fluid is extracted from the wellbore;
determining, based on the error function, an oil water ratio of the drilling fluid and an average specific gravity of the drilling fluid periodically or continuously during a drilling operation; and
providing the oil water ratio of the drilling fluid and an average specific gravity of the drilling fluid to an operator during the drilling operation.

14. The non-transitory computer-readable medium of claim 13, wherein the one or more instructions, which when executed by the processor cause the processor to perform operations comprising:
obtaining a second mud density of the drilling fluid;

obtaining a second measurement of the thermal conductivity of the drilling fluid;

determining a second error function of a second calculation of characteristics of the drilling fluid, wherein the second error function is indicative of a threshold difference between the second calculation of the characteristics of the drilling fluid and the characteristics of the drilling fluid obtained through the retort data of the mud distillation process; and determining, based on the error function, a second oil water ratio of the drilling fluid and a second average specific gravity of the drilling fluid.

15. The system of claim 10, wherein the one or more processors are further configured to: determine a base oil type of an oil used in the drilling fluid, wherein the oil is one component of the plurality of components of the drilling fluid.

16. The non-transitory computer-readable medium of claim 13, wherein the one or more instructions, which when executed by the processor cause the processor to perform operations comprising: determining a base oil type of an oil used in the drilling fluid, wherein the oil is one component of the plurality of components of the drilling fluid.

17. The system of claim 10, wherein the components of the drilling fluid comprise oil, water, brine, and barite, and wherein obtaining the thermal conductivity of each component of the drilling fluid comprises obtaining the thermal conductivity of oil, water, brine, and barite.

18. The non-transitory computer-readable medium of claim 13, wherein the components of the drilling fluid comprise oil, water, brine, and barite, and wherein obtaining the thermal conductivity of each component of the drilling fluid comprises obtaining the thermal conductivity of oil, water, brine, and barite.

19. The system of claim 10, wherein the oil water ratio of the drilling fluid and the average specific gravity of the drilling fluid are dynamically determined during a drilling process where the drilling fluid is pumped into the wellbore.

20. The non-transitory computer-readable medium of claim 13, wherein the oil water ratio of the drilling fluid and the average specific gravity of the drilling fluid are dynamically determined during a drilling process where the drilling fluid is pumped into the wellbore.

* * * * *